(12) United States Patent
Reiderman et al.

(10) Patent No.: US 10,422,759 B2
(45) Date of Patent: Sep. 24, 2019

(54) GRADIENT MULTI-FREQUENCY NUCLEAR MAGNETIC RESONANCE WITH INTER-BAND INTERFERENCE

(71) Applicant: Halliburton Energy Services, Inc., Houston, TX (US)

(72) Inventors: Arcady Reiderman, Katy, TX (US); Shriram Sarvotham, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 86 days.

(21) Appl. No.: 15/121,610

(22) PCT Filed: Aug. 14, 2015

(86) PCT No.: PCT/US2015/045203
§ 371 (c)(1),
(2) Date: Aug. 25, 2016

(87) PCT Pub. No.: WO2017/030523
PCT Pub. Date: Feb. 23, 2017

(65) Prior Publication Data
US 2017/0176360 A1    Jun. 22, 2017

(51) Int. Cl.
*G01V 3/00* (2006.01)
*G01N 24/08* (2006.01)
(Continued)

(52) U.S. Cl.
CPC .......... *G01N 24/081* (2013.01); *E21B 49/00* (2013.01); *G01R 33/448* (2013.01); *G01V 3/32* (2013.01)

(58) Field of Classification Search
CPC ... G01V 3/28; G01V 3/38; G01V 3/18; G01V 3/20; G01V 3/22; G01V 3/24; G01V 3/26;
(Continued)

(56) References Cited

U.S. PATENT DOCUMENTS 6,597,170 B1    7/2003 Beard et al.
7,663,363 B2 *  2/2010 Reiderman .......... G01N 24/081
                                              324/303
(Continued)

FOREIGN PATENT DOCUMENTS

WO    2015/072985 A1    5/2015

OTHER PUBLICATIONS

ISR/WO for PCT/US2015/045203 dated Apr. 26, 2016.
European Application Serial No. 15901806.8; European Search Report; dated Feb. 22, 2019, 9 pages.

*Primary Examiner* — Thang X Le
(74) *Attorney, Agent, or Firm* — Gilliam IP PLLC

(57) ABSTRACT

NMR logging of hydrocarbon formations may be performed with a gradient multi-frequency NMR technique using an increased packing density of the sensitive volumes such that the radiofrequency (RF) pluses for adjacent sensitive volumes interfere. An exemplary method may include applying first and second sequences of RF pulses at first and second frequencies, respectively, the second sequence being applied at a time interval following the first sequence; acquiring the NMR relaxation data from first and second sensitive volumes corresponding to the first and second frequencies, respectively; and selecting the first and second frequencies and the time interval to allow for interference between the first sequence of RF pulses and the NMR relaxation data from the second sensitive volume in order to increase a
(Continued)

signal-to-noise ratio and a signal-to-noise ratio per square root of time of the NMR relaxation data.

19 Claims, 7 Drawing Sheets

(51) Int. Cl.
    *G01R 33/44*     (2006.01)
    *E21B 49/00*     (2006.01)
    *G01V 3/32*     (2006.01)

(58) Field of Classification Search
    CPC . G01V 3/30; G01V 3/10; G01V 3/265; G01V 3/02; G01V 3/04; G01V 3/06; G01V 3/104
    See application file for complete search history.

(56) References Cited

U.S. PATENT DOCUMENTS

| | | | |
|---|---|---|---|
| 9,632,204 B2* | 4/2017 | Jachmann | G01V 3/32 |
| 2002/0175681 A1* | 11/2002 | Taicher | G01V 3/32 |
| | | | 324/303 |
| 2002/0175682 A1 | 11/2002 | Chen et al. | |
| 2003/0001569 A1* | 1/2003 | Chen | G01R 33/50 |
| | | | 324/303 |
| 2003/0071617 A1 | 4/2003 | Kruspe et al. | |
| 2003/0132749 A1 | 7/2003 | Speier et al. | |
| 2004/0008027 A1* | 1/2004 | Prammer | G01N 24/081 |
| | | | 324/303 |
| 2004/0017193 A1* | 1/2004 | Speier | G01N 24/081 |
| | | | 324/303 |
| 2004/0090230 A1* | 5/2004 | Appel | G01N 24/081 |
| | | | 324/307 |
| 2004/0257074 A1* | 12/2004 | Appel | G01V 3/32 |
| | | | 324/303 |
| 2005/0162162 A1* | 7/2005 | Itskovich | G01V 3/32 |
| | | | 324/303 |
| 2009/0066327 A1 | 3/2009 | Chen | |
| 2013/0093422 A1 | 4/2013 | Morys et al. | |
| 2013/0234704 A1* | 9/2013 | Hurlimann | G01N 24/081 |
| | | | 324/303 |
| 2013/0234705 A1* | 9/2013 | Mandal | G01N 24/081 |
| | | | 324/303 |
| 2015/0035531 A1 | 2/2015 | Stemmer | |
| 2015/0061664 A1 | 3/2015 | Reiderman et al. | |
| 2015/0061665 A1 | 3/2015 | Reiderman et al. | |

* cited by examiner

GRADIENT MULTI-FREQUENCY NUCLEAR MAGNETIC RESONANCE WITH INTER-BAND INTERFERENCE

BACKGROUND

The present application relates to nuclear magnetic resonance (NMR) logging of subterranean formations.

Well logging is a common practice in the oil and gas industry to evaluate underground formations for the presence and producibility of subterranean formations. Among the most important parameters determined in the process are the depth and thickness of formation layers containing hydrocarbon, the formation porosity (i.e., the relative amount of void space in the formation), the hydrocarbon saturation (i.e., the relative percentage of hydrocarbons versus water in the pore space), and the permeability of the formation (i.e., the ability of the oil, gas, or water to flow out of the formation, into the well and eventually to the surface for recovery).

Presently, NMR logging is considered to be one of the most effective techniques for determining these geologic parameters. NMR technology has many advantages over other logging techniques (such as gamma ray logging, sonic logging, electric logging, and others), one of the most significant being the independence of NMR measurements from formation lithology. In particular, NMR data relates in a simple manner to formation pore sizes. This relationship facilitates detection of formation fluids (e.g., gas, oil, and water) independent of the matrix mineralogy. To this end, in addition to estimation of formation porosity, hydrocarbon saturation, and permeability, NMR logging enables computation of clay-bound water, capillary-bound water, and free fluid volumes, which aid in comprehensively evaluating the subterranean formation.

NMR logging used for evaluating subterranean formations typically includes a Carr-Purcell-Meiboom-Gill (CPMG) pulse sequence, which is a sequence of radio-frequency (RF) pulses producing NMR spin echoes that decay with time. The decay time is used to calculate the NMR relaxation data (e.g., the spin-spin relaxation time (T2)). The CPMG pulse sequence comprises one excitation RF pulse and a plurality of refocusing RF pulses. The refocusing RF pulses in the plurality of refocusing pulses of the CPMG pulse sequence are spaced by a time interval (TE). Nuclear spin echoes produced by the refocusing pulses are spaced by the same time interval TE, which is referred to as "echo spacing." Therefore, it is advantageous to reduce the TE to a minimum possible value in order to produce larger number of echoes per unit time and achieve higher signal to noise ratio (SNR) per unit time. One of the limiting factors in achieving shorter TE is the refocusing pulse width.

Most NMR logging use a gradient static magnetic field and employ multi-frequency measurements, which is referred to herein as gradient multi-frequency NMR. Gradient multi-frequency NMR techniques use CPMG pulse sequences at different frequencies to investigate different volumes of the subterranean formation at various radial distances from the wellbore, which in effect are concentric cylinders radiating from the wellbore. As used herein, the term "sensitive volume" refers to the volume of the formation investigated by NMR. The thickness of the sensitive volumes is determined by the bandwidth of the refocusing RF pulse.

Because gradient multi-frequency NMR techniques use a different excitation frequency to investigate each sensitive volume, multiple sensitive volumes can be interrogated while waiting for the nuclear magnetization in the first sensitive volume to recover its equilibrium state. As a result, the total signal acquired per unit time for the gradient multi-frequency NMR techniques may be increased by a factor of 5-10 over single-frequency techniques where each sensitive volume must be interrogated separately and sequentially. Additionally, the gradient multi-frequency NMR techniques may advantageously identify the formation fluid type and provide a profile of saturation in a single pass.

The multiple frequencies, typically 5-10, used in a gradient multi-frequency NMR technique to interrogate different sensitive volumes need to fit in an operating frequency range. This operating frequency range and, more specifically, the upper and lower operating frequencies define the volume of the formation that could potentially be interrogated. Maximum depth of investigation, for a given magnet configuration, determines the operating frequency range. Individual operating frequencies determine the distance of the corresponding sensitive volumes from the tool sensor. The farther the sensitive volume from the tool the less the signal induced in the NMR antenna.

One of the challenges of fitting the multiple frequency bands in the operating frequency range is the interference between adjacent frequency bands due to out-of-band parts of the RF pulse spectrum. The out-of-band parts interfere with adjacent frequency bands by distorting equilibrium state of nuclear magnetization in the neighborhood of the excitation band. To decrease the interference, the sensitive volumes interrogated are spaced apart, typically, by 3 times the sensitive volume thickness. Accordingly, a significant portion of the formation volume around the wellbore is not investigated and analyzed.

One strategy for addressing interference and increasing the volume interrogated is to change the shape of the RF pulses, which essentially suppresses the out-of-band parts of the RF pulse spectrum. In some instances, the shape of the RF pulses is changed from simple rectangular pulses to complex non-rectangular pulses (e.g., Hann pulses). However, using pulse-shaping techniques only increases the volume of the formation interrogated to about 30-50% of the volume that could be interrogated as defined by the operating frequency range.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present application relates to NMR logging of hydrocarbon formations and, more specifically, to a gradient multi-frequency NMR technique that further increases the volume of the formation interrogated by increasing the packing density of the sensitive volumes.

In the embodiments described herein, the thickness and spacing of the sensitive volumes may be selected such that the RF pluses for adjacent sensitive volumes interfere. To address the interference, some embodiments of the present application increase the SNR and, more importantly, the SNR per square root time (SNR/√time). Additionally, it has been discovered that the interference may, in some embodiments, be used to analyze the diffusion of fluids in the sensitive volumes and the permeability of the formation.

Figure 1:
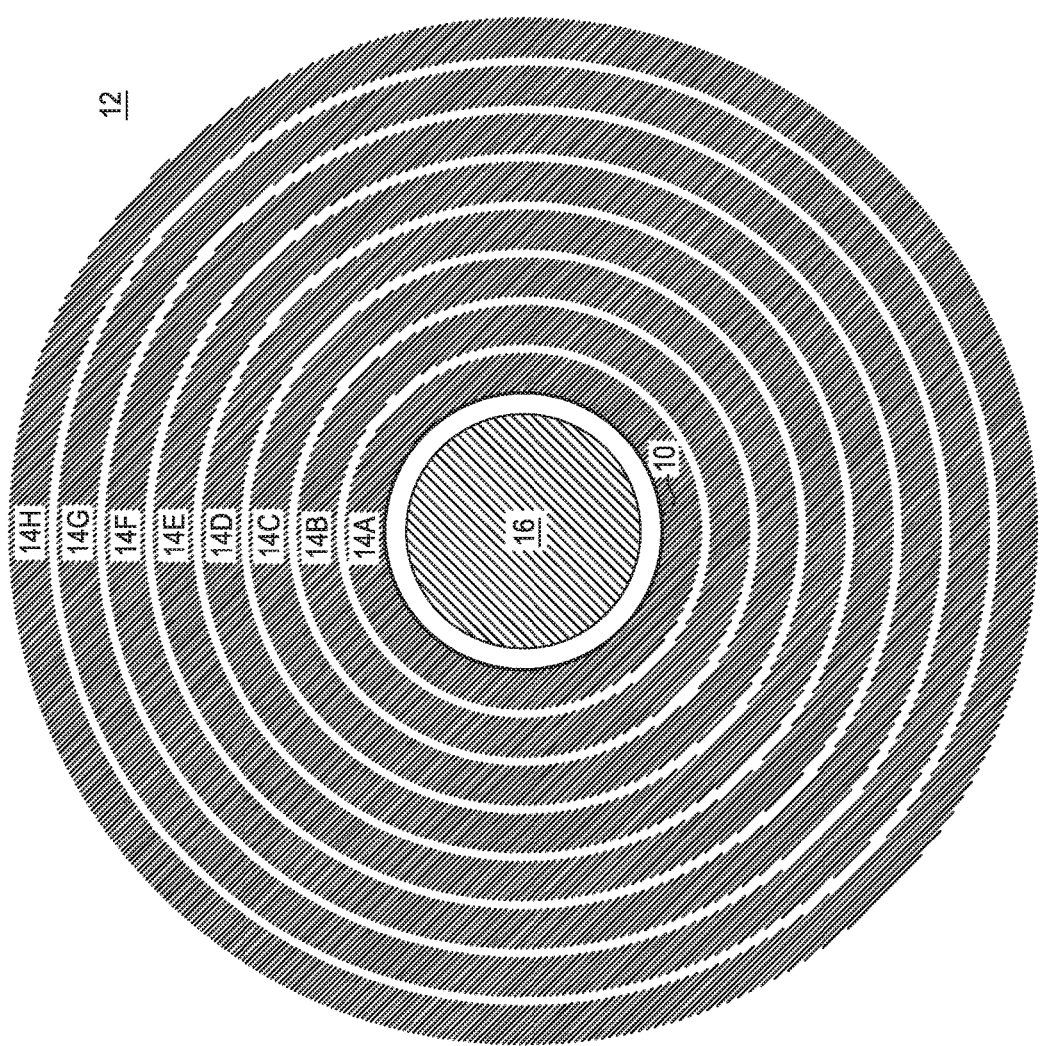
FIG. 1 illustrates a cross-sectional top view of a wellbore and a surrounding subterranean formation with eight concentric sensitive volumes of a gradient multi-frequency NMR procedure, according to at least some embodiments described herein.

FIG. 1 illustrates a cross-sectional top view of a wellbore 10 and a surrounding subterranean formation 12 with eight concentric sensitive volumes 14A-H of a gradient multi-frequency NMR procedure, according to at least some embodiments described herein. The sensitive volumes 14A-H may comprise excitation volumes (i.e., excitation bands) in a multi-frequency gradient NMR measurement. When the gradient multi-frequency NMR procedure is performed with an NMR logging tool 16 disposed in the wellbore 10, methods may involve acquiring NMR relaxation data for each of the sensitive volumes 14A-H. While eight sensitive volumes 14A-H are illustrated, one skilled in the art would recognize that other numbers of sensitive volumes (e.g., 4 to 14) may be interrogated and analyzed by the method described herein.

A gradient multi-frequency NMR procedure described herein may involve applying a sequence of RF pulses at two or more frequencies where each frequency corresponds to a sensitive volume 14A-H. In some embodiments, the sequence of RF pulse may be performed in order of descending frequency, which sequentially interrogates from the sensitive volume 14A nearest to the NMR tool 16 to the sensitive volume 14H furthest from the NMR tool 16. In some instances, each of the RF pulses may be a CPMG pulse sequence. Then, the NMR logging tool may acquire the NMR relaxation data corresponding to each of the applied RF pulses (e.g., the time associated with spin echo decay for CPMG pulse sequences, which is related to T2).

The volume of the subterranean formation interrogated by NMR relative to the total volume corresponding to the operating frequency range is referred to herein as the "band filling factor," which is also defined as the ratio $\Delta f_p/\Delta f_b$, where $\Delta f_p$ is the refocusing pulse bandwidth and $\Delta f_b$ is the frequency separation between the centers of the adjacent RF pulse bands. The band filling factor multiplied by 100 represents a percentage of the volume interrogated. In the embodiments described herein, interference is preferred because it has been discovered that a significant enhancements in SNR and SNR/√time can be achieved as well as additional data can be gleaned from the interference, each of which is described in more detail below. In some instances, the band filling factor may be about 0.3 to about 1.0 including subsets therebetween (e.g., about 0.4 to about 1.0, about 0.5 to about 1.0, about 0.6 to about 1.0, and about 0.7 to about 1.0).

As described previously, the RF pulse used to generate the NMR relaxation data for each sensitive volume 14A-H interfere with adjacent NMR relaxation data, which decreases the NMR relaxation data signal strength and is why previous methods have mitigated inter-band interference. However, the present application seeks to increase SNR and SNR/√time for the NMR relaxation data, which may be achieved by increasing the band filling factor and, consequently, causing more inter-band interference. Accordingly, the methods described herein involve selecting the frequency of the RF pluses and the time between the RF pulses to provide for inter-band interference to increase the SNR and SNR/√time of the NMR relaxation data.

In some embodiments, signal density (i.e., the number and occurrence of RF pulses) may be increased, which may lead to increased SNR/√time. One method of increasing signal density is using rectangular pulses, which are shorter than non-rectangular pulses and can be applied more frequently.

In another method to achieve greater signal density for rectangular or non-rectangular RF pulses, each RF pulse (e.g., each CPMG pulse sequence) corresponding to different sensitivity volumes may, in some instances, be started immediately following the previous RF pulse (e.g., previous CPMG pulse sequence) ends. Further, after interrogation of the farthest sensitive volume 14H, the sequence of RF pulses may be repeated starting with the nearest sensitive volume 14A. In some instances, a sufficient time may pass before repetition of the sequence of RF pulses such that the distortion of the equilibrium state of the nuclear magnetization (i.e., the interference) in the nearest sensitive volume 14A due to excitation in the second sensitive volume 14B is insignificant. That is, the time passed from the end of the RF pulse of second sensitive volume 14B to the start of the RF pulse of nearest sensitive volume 14A is nearly the time needed for a full recovery of the equilibrium state of nuclear magnetization in the nearest sensitive volume 14A. Therefore, the inter-band interference has negligible effect on the nearest sensitive volume 14A, which increases the accuracy of measurements as well as the SNR and the SNR/√time.

Because the inter-band interference depends on molecular diffusion of the fluid in the formation, a comparison of the nearest sensitive volume 14A signal to the signals (or integrated signals) from the other sensitive volumes 14B-H may be used to assess the diffusion rate(s) of the fluid(s) in the subterranean formation 12. Diffusion rate assessment may be performed by comparing of the NMR relaxation signal amplitudes obtained from the region 14A, which is unaffected by the inter-band interference, with the signal amplitudes obtained from other regions that are affected by the interference and, therefore, by the diffusion rate. The diffusion rate averaged over the time of a CPMG train corresponds essentially to restricted diffusion process in the porous media of the subterranean formations and, therefore, is characteristic of the permeability of the subterranean formations.

Figure 2:
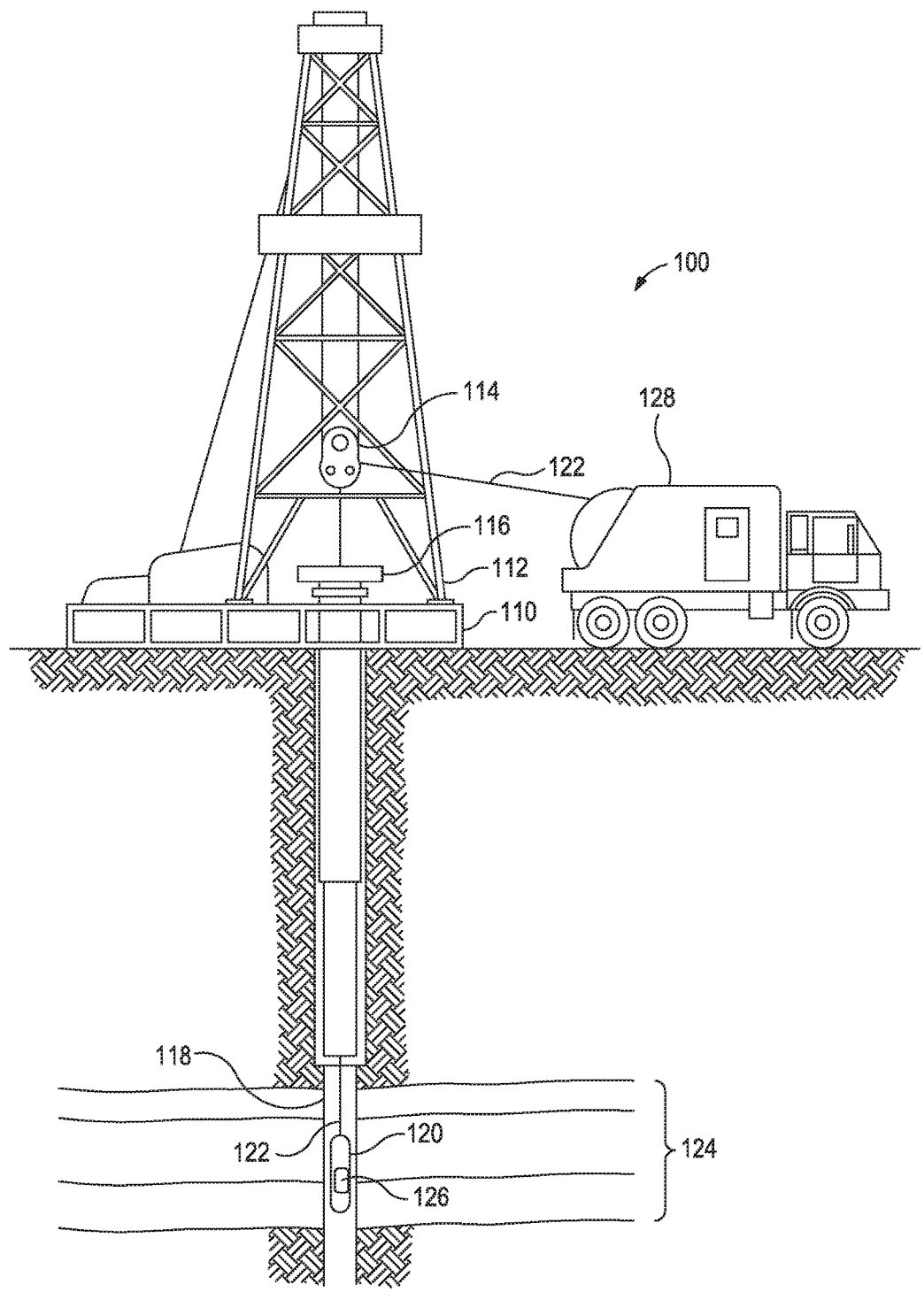
FIG. 2 illustrates a wireline system suitable for performing gradient multi-frequency NMR procedure downhole according to various embodiments described herein.

As described previously, the inter-band interference is affected by diffusion of the fluid being analyzed and movement of the NMR logging tool. Movement of the NMR logging tool results in movement of the magnetic field relative to the fluid in the formation. Some embodiments may involve measuring the motion of the NMR logging tool with one or more sensors that measure velocity and acceleration and are coupled to the NMR logging tool. Examples of suitable sensors may include, but are not limited to, gyroscopes, accelerometers, and the like. The lateral motion of the NMR logging tool as derived from the velocity and acceleration of the NMR logging tool may then be used for deriving a tool motion correction that may be applied to the NMR relaxation data to improve the accuracy of the data. This can be done, for example, by removing noise that is correlated with a motional sensor reading from a set of NMR data. FIG. 2 is a wireline system 100 suitable for performing gradient multi-frequency NMR procedure downhole, according to various embodiments described herein. As illustrated, a drilling platform 110 may be equipped with a derrick 112 that supports a hoist 114. Drilling oil and gas wells are commonly carried out using a string of drill pipes connected together so as to form a drilling string that is lowered through a rotary table 116 into a wellbore 118. Here, it is assumed that the drilling string has been temporarily removed from the wellbore 118 to allow an NMR logging tool 120 to be lowered by wireline or logging cable 122 into the wellbore 118. Typically, the NMR logging tool 120 is lowered to a region of interest and subsequently pulled upward at a substantially constant speed. During the upward trip, instruments included in the NMR logging tool 120 may be used to perform measurements on the subterranean formation 124 adjacent the wellbore 118 as the NMR logging tool 120 passes by. As illustrated, the NMR logging tool 120 includes a motion sensor 126 described herein.

The NMR relaxation data and data from the motion sensor 126 may be communicated to a logging facility 128 for storage, processing, and analysis. The logging facility 128 may be provided with electronic equipment for various types of signal processing.

In some instances, the NMR logging tool 120 may be adapted for connection to a drill pipe for performing logging-while-drilling (LWD) using the gradient multi-frequency NMR procedures described herein.

Figure 3:
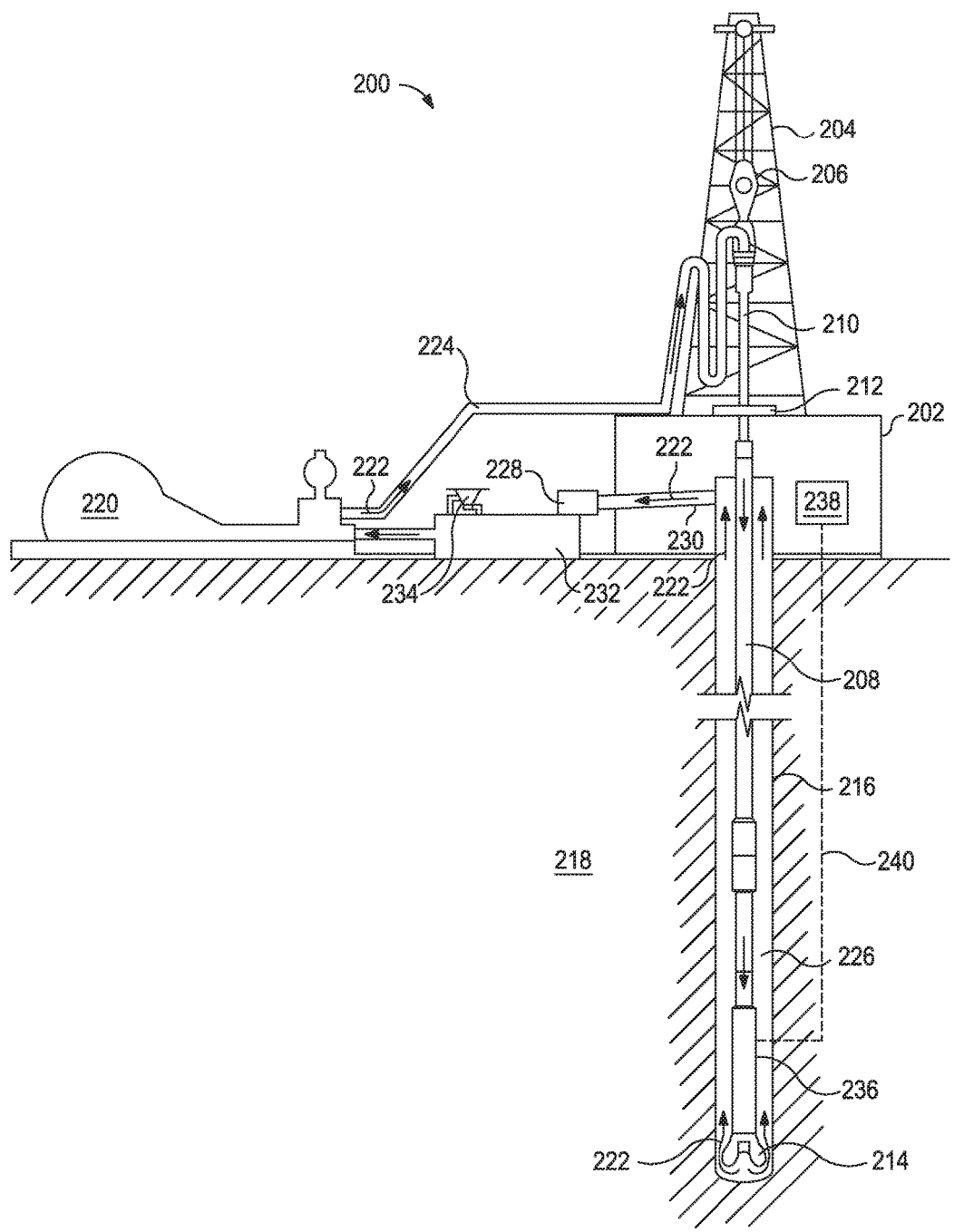
FIG. 3 illustrates an exemplary drilling assembly suitable for implementing the LWD tools describe herein.

FIG. 3 illustrates an exemplary drilling assembly suitable for performing gradient multi-frequency NMR procedure downhole, according to various embodiments described herein. It should be noted that while FIG. 3 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 200 may include a drilling platform 202 that supports a derrick 204 having a traveling block 206 for raising and lowering a drill string 208. The drill string 208 may include, but is not limited to, drill pipe and coiled tubing, as generally known to those skilled in the art. A kelly 210 supports the drill string 208 as it is lowered through a rotary table 212. A drill bit 214 is attached to the distal end of the drill string 208 and is driven either by a downhole motor and/or via rotation of the drill string 208 from the well surface. As the bit 214 rotates, it creates a wellbore 216 that penetrates various subterranean formations 218. Along the drill string 208, a NMR logging tool 236 (also referred to as LWD tool 236) described herein is included.

In the present application, the LWD tool 236 may be capable of performing gradient multi-frequency NMR procedures and optionally include a motion sensor (not illustrated but similar to the motion sensor 126 of FIG. 2) for measuring the velocity and acceleration of the LWD tool 236. The LWD tool 236 and motion sensor may transmit the measured data wired or wirelessly to a processor 238 at the surface. Transmission of the data is generally illustrated at line 240 to demonstrate communicable coupling between the processor 238 and the LWD tool 236 and does not necessarily indicate the path to which communication is achieved.

A pump 220 (e.g., a mud pump) circulates drilling fluid 222 through a feed pipe 224 and to the kelly 210, which conveys the drilling fluid 222 downhole through the interior of the drill string 208 and through one or more orifices in the drill bit 214. The drilling fluid 222 is then circulated back to the surface via an annulus 226 defined between the drill string 208 and the walls of the wellbore 216. At the surface, the recirculated or spent drilling fluid 222 exits the annulus 226 and may be conveyed to one or more fluid processing unit(s) 228 via an interconnecting flow line 230. After passing through the fluid processing unit(s) 228, a "cleaned" drilling fluid 222 is deposited into a nearby retention pit 232 (i.e., a mud pit). While illustrated as being arranged at the outlet of the wellbore 216 via the annulus 226, those skilled in the art will readily appreciate that the fluid processing unit(s) 228 may be arranged at any other location in the drilling assembly 200 to facilitate its proper function, without departing from the scope of the scope of the disclosure.

Chemicals, fluids, additives, and the like may be added to the drilling fluid 222 via a mixing hopper 234 communicably coupled to or otherwise in fluid communication with the retention pit 232. The mixing hopper 234 may include, but is not limited to, mixers and related mixing equipment known to those skilled in the art. In other embodiments, however, the chemicals, fluids, additives, and the like may be added to the drilling fluid 222 at any other location in the drilling assembly 200. In at least one embodiment, for example, there could be more than one retention pit 232, such as multiple retention pits 232 in series. Moreover, the retention pit 232 may be representative of one or more fluid storage facilities and/or units where the chemicals, fluids, additives, and the like may be stored, reconditioned, and/or regulated until added to the drilling fluid 222.

The processor 238 may comprise a portion of computer hardware used to implement the various illustrative blocks, modules, elements, components, methods, and algorithms for analyzing the measurements described herein. The processor 238 may be configured to execute one or more sequences of instructions, programming stances, or code stored on a non-transitory, computer-readable medium. The processor 238 can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor 238 to perform the process steps to analyze the measurements described herein. One or more processors 238 in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to the processor 238 for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include Embodiment A, Embodiment B, and Embodiment C.

Embodiment A is a method that includes performing a gradient multi-frequency NMR procedure with an NMR logging tool disposed in a wellbore penetrating a subterranean formation and thereby obtaining NMR relaxation data, the gradient multi-frequency NMR procedure comprising: applying a first sequence of RF pulses at a first frequency; acquiring the NMR relaxation data corresponding to a first sensitive volume of the subterranean formation; applying a second sequence of RF pulses at a second frequency corresponding to a second sensitive volume of the subterranean formation, the second sequence being applied at a time interval following the first sequence; acquiring the NMR relaxation data corresponding to the second sensitive volume of the subterranean formation; and selecting the first and second frequencies and the time interval to allow for interference between the first sequence of RF pulses and the NMR relaxation data from the second sensitive volume in order to increase a signal-to-noise ratio and a signal-to-noise ratio per square root of time of the NMR relaxation data.

Embodiment A may have one or more of the following additional elements in any combination: Element 1: the method further including measuring tool motion with a sensor coupled to the NMR logging tool; calculating a tool motion correction based on the tool motion; and applying the tool motion correction to the NMR relaxation data; Element 2: wherein the first sequence and the second sequence of RF pulses comprise rectangular RF pulses with a band filling factor of about 0.5 to about 1.0; Element 3: wherein the first sequence and the second sequence of RF pulses comprise non-rectangular RF pulses with a band filling factor of about 0.6 to about 1.0; Element 4: wherein the first sequence and the second sequence of RF pulses are CPMG pulse sequences; Element 5: the method further including comparing an amplitude of the NMR relaxation data corresponding to the first and second sensitive volumes; and calculating a permeability of the subterranean formation; Element 6: wherein the time interval is a first time interval and the method further comprises: applying a third sequence of RF pulses at a third frequency corresponding to a third sensitive volume of the subterranean formation, the third sequence being applied at a second time interval following the second sequence; acquiring the NMR relaxation data corresponding to the third sensitive volume of the subterranean formation; and selecting the second and third frequencies and the second time interval to allow for interference between the second sequence of RF pulses and the NMR relaxation data from the third sensitive volume in order to increase a signal-to-noise ratio and a signal-to-noise ratio per square root of time of the NMR relaxation data; Element 7: Element 6 and the method further including comparing an amplitude of the NMR relaxation data corresponding to the first and third sensitive volumes; and calculating a permeability of the subterranean formation; Element 8: Element 6 and wherein the first, second, and third sequences of RF pulses comprise rectangular RF pulses with a band filling factor of about 0.5 to about 1.0; and Element 9: Element 6 and wherein the first, second, and third sequences of RF pulses comprise non-rectangular RF pulses with a band filling factor of about 0.6 to about 1.0.

By way of non-limiting example, exemplary combinations applicable to Embodiment A include: Element 1 in combination with Element 2 or Element 3; Element 1 in combination with one or more of Elements 4-7; Element 1 in combination with Element 6 and either Element 8 or Element 9; Element 2 or Element 3 in combination with one or both of Elements 4-5; Element 4 in combination with one or more of Elements 5-7 and optionally either Element 8 or Element 9; Element 5 in combination with one or both of Elements 6-7 and optionally either Element 8 or Element 9; and Element 6 in combination Element 7 and optionally either Element 8 or Element 9.

Embodiment B is a method that includes performing a gradient multi-frequency NMR procedure with an NMR logging tool disposed in a wellbore penetrating a subterranean formation and thereby obtaining NMR relaxation data, the gradient multi-frequency NMR procedure comprising: applying a sequence of rectangular RF pulses at two or more frequencies with a band filling factor of about 0.5 to about 1.0, each of the frequencies corresponding to a sensitive volume, and repeating the sequence of rectangular RF pulses.

Embodiment C is a method that includes performing a gradient multi-frequency NMR procedure with an NMR logging tool disposed in a wellbore penetrating a subterranean formation and thereby obtaining NMR relaxation data, the gradient multi-frequency NMR procedure comprising: applying a sequence of non-rectangular RF pulses at two or more frequencies with a band filling factor of about 0.6 to about 1.0, each of the frequencies corresponding to a sensitive volume, and repeating the sequence of non-rectangular RF pulses.

Embodiments B and C may have one or more of the following additional elements in any combination: Element 10: wherein applying the sequence of non-rectangular RF pulse sequences includes a CPMG pulse sequence at each of the frequencies; Element 11: the method further including measuring tool motion with a sensor coupled to the NMR logging tool; calculating a tool motion correction based on the tool motion; and applying the tool motion correction to the NMR relaxation data; and Element 12: comparing an amplitude of the NMR relaxation data corresponding to a first volume and a second sensitive volume; and calculating a permeability of the subterranean formation.

By way of non-limiting example, exemplary combinations applicable to Embodiment B include: Element 10 in combination with Element 11 and optionally Element 12; Element 10 in combination with Element 12; and Element 11 in combination with Element 12.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

Examples

To test the methods described herein, several numerical simulations were performed.

In a first simulation, a gradient multi-frequency NMR procedure was simulated with a shaped (Hann) refocusing pulse, having a variable pulse duration (to produce variable frequency band filling factor) with minimum pulse duration 50 μs, and a 40 Gauss/cm gradient of the static magnetic field. In this simulation, two scenarios were considered: no molecular diffusion and water diffusion.

Figure 4:
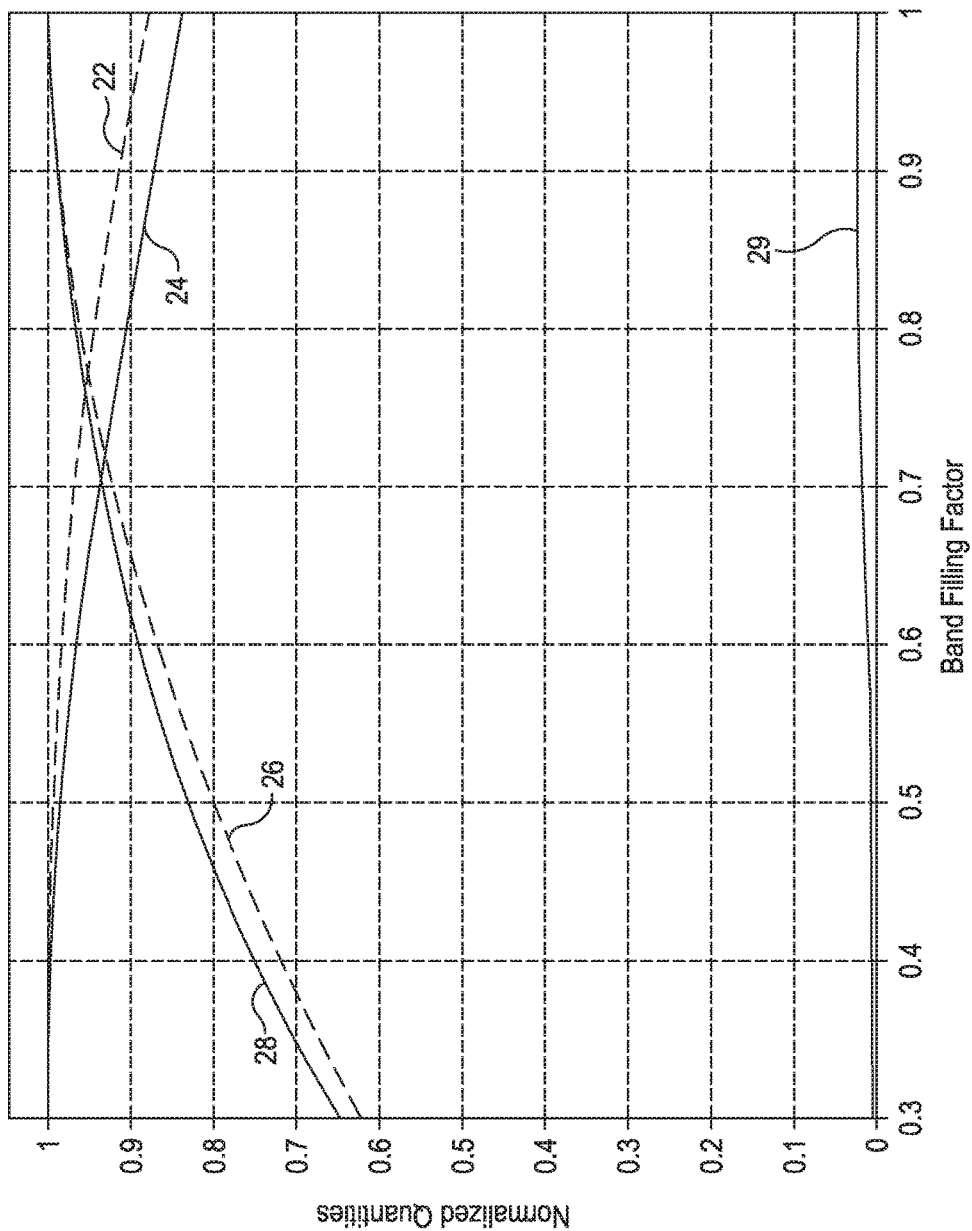
FIG. 4 provides normalized plots of a numerical simulation result for the NMR signal amplitudes and signal to noise ratio (SNR) each as a function of the band filling factor.
Figure 5:
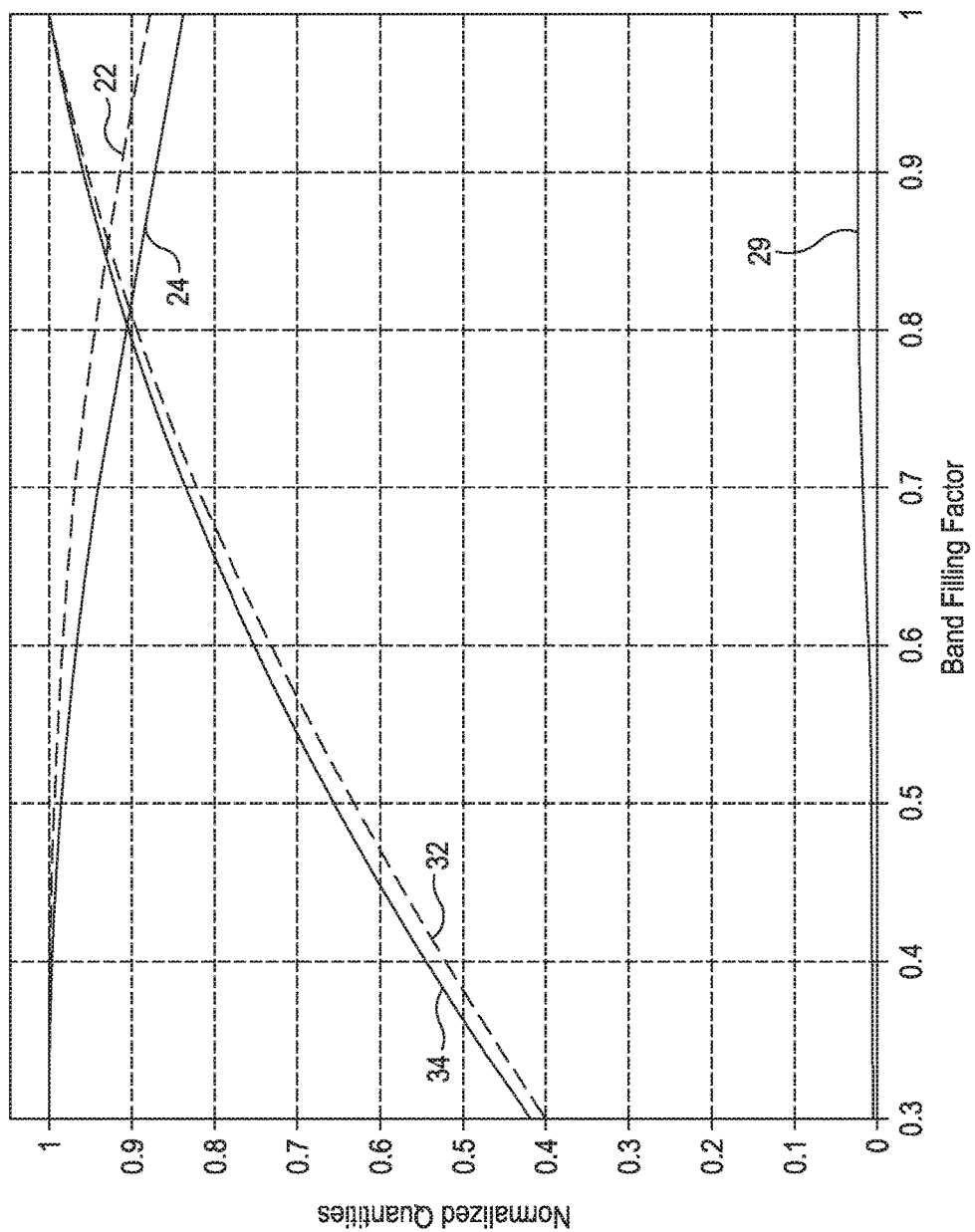
FIG. 5 provides normalized plots of a numerical simulation result for the SNR and SNR/√time each as a function of the band filling factor.

FIGS. 4 and 5 provide the numerical simulation results for normalized plots of the NMR signal amplitudes (plot 22 (no molecular diffusion) and plot 24 (water diffusion)), SNR (plot 26 (no molecular diffusion) and plot 28 (water diffusion)), and SNR/√time (plot 32 (no molecular diffusion) and plot 34 (water diffusion)), each as a function of the band filling factor.

The NMR signal data at 22 and 24 correspond to a practical diffusion range for most formation fluids. Therefore, the uncertainty in the NMR signal amplitudes due to unknown diffusion coefficient is determined by the difference between these two curves. As seen in FIG. 4 the NMR signal reduction with increasing the band filling factor to 1 is 12-16% (depending on diffusion). As described herein, the average signal reduction corresponding to a particular band filling factor may be accounted for by calibration using a calibration fluid with a known self-diffusion coefficient. Remaining error of the NMR signal measurement (directly affecting porosity measurement error) is in this case associated with the diffusion uncertainty. This error as a function of band filling factor is shown in FIG. 4 at 29. Additional error reduction may be achieved by introducing a diffusion correction based on a set of multi-frequency measurements. The diffusion measurements typically do not require accurate NMR signal readings but rather use accurate measurement of changes of the NMR signal when changing parameters of the CPMG (CPMG-like) pulse sequence or/and doing measurements at different static magnetic field gradients Plots 26,28 and 32,34 (FIG. 5) demonstrate that, for this numerical simulation, increasing band packing density from practically no interference to significant interference yields a 15% and 40% increase SNR and SNR/√time, respectively.

A second numerical model, which is similar to the first, uses a square refocusing pulse with minimum pulsed duration 25 μs and a 40 Gauss/cm gradients. This represents the methods described herein using rectangular shape pulses and shorter pulse spacing to reduce interference.

Figure 6:
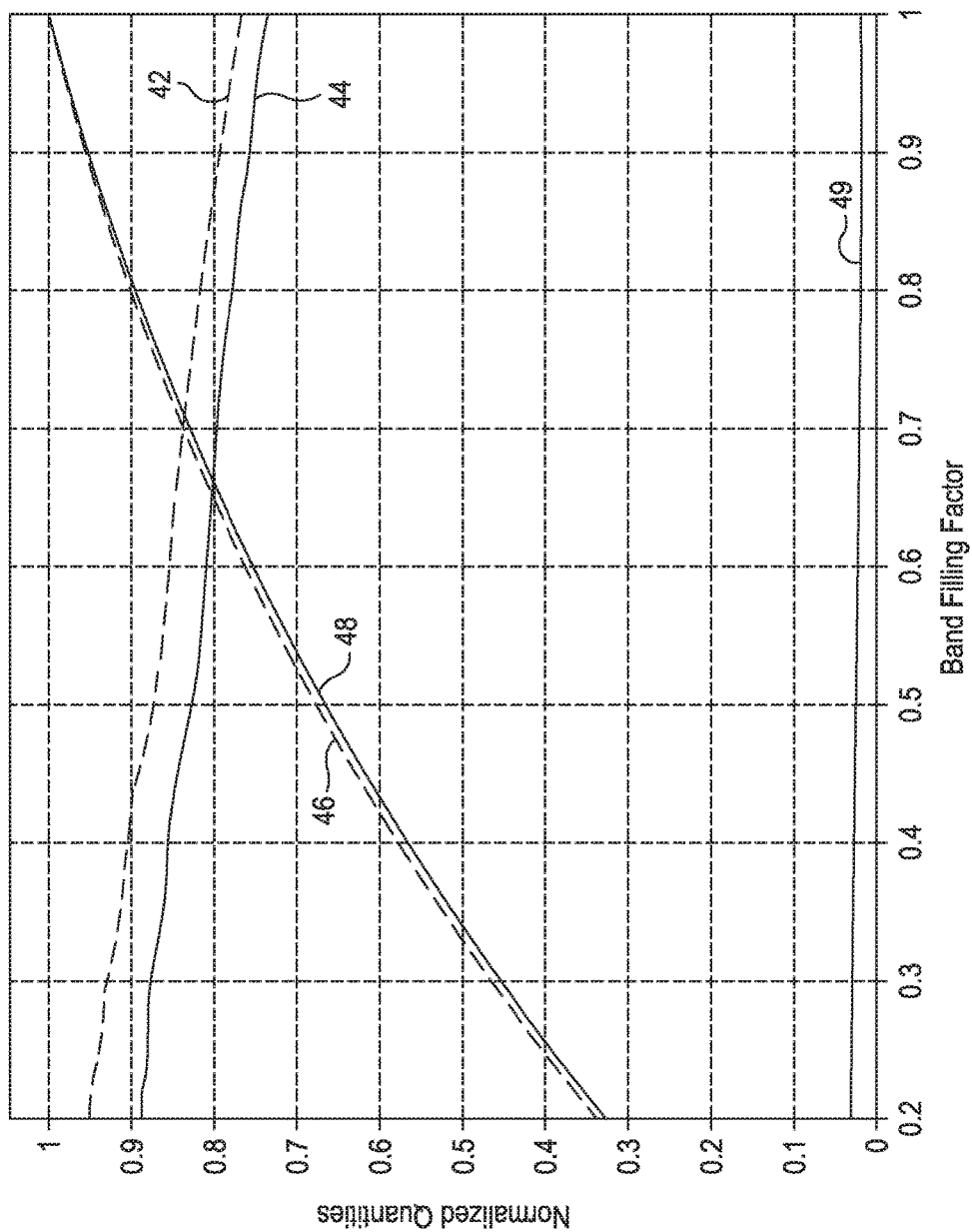
FIG. 6 provides normalized plots of a numerical simulation result for the NMR signal amplitudes and SNR/√time each as a function of the band filling factor.

FIG. 6 provides the numerical simulation results for normalized plots of the NMR signal amplitudes (plot 42 (no molecular diffusion) and plot 44 (water diffusion)) and SNR/√time (plot 46 (no molecular diffusion) and plot 48 (water diffusion)), each as a function of the band filling factor.

The effect of tighter band packing is shown to cause more than a 50% increase in SNR/√time ratio.

Figure 7:
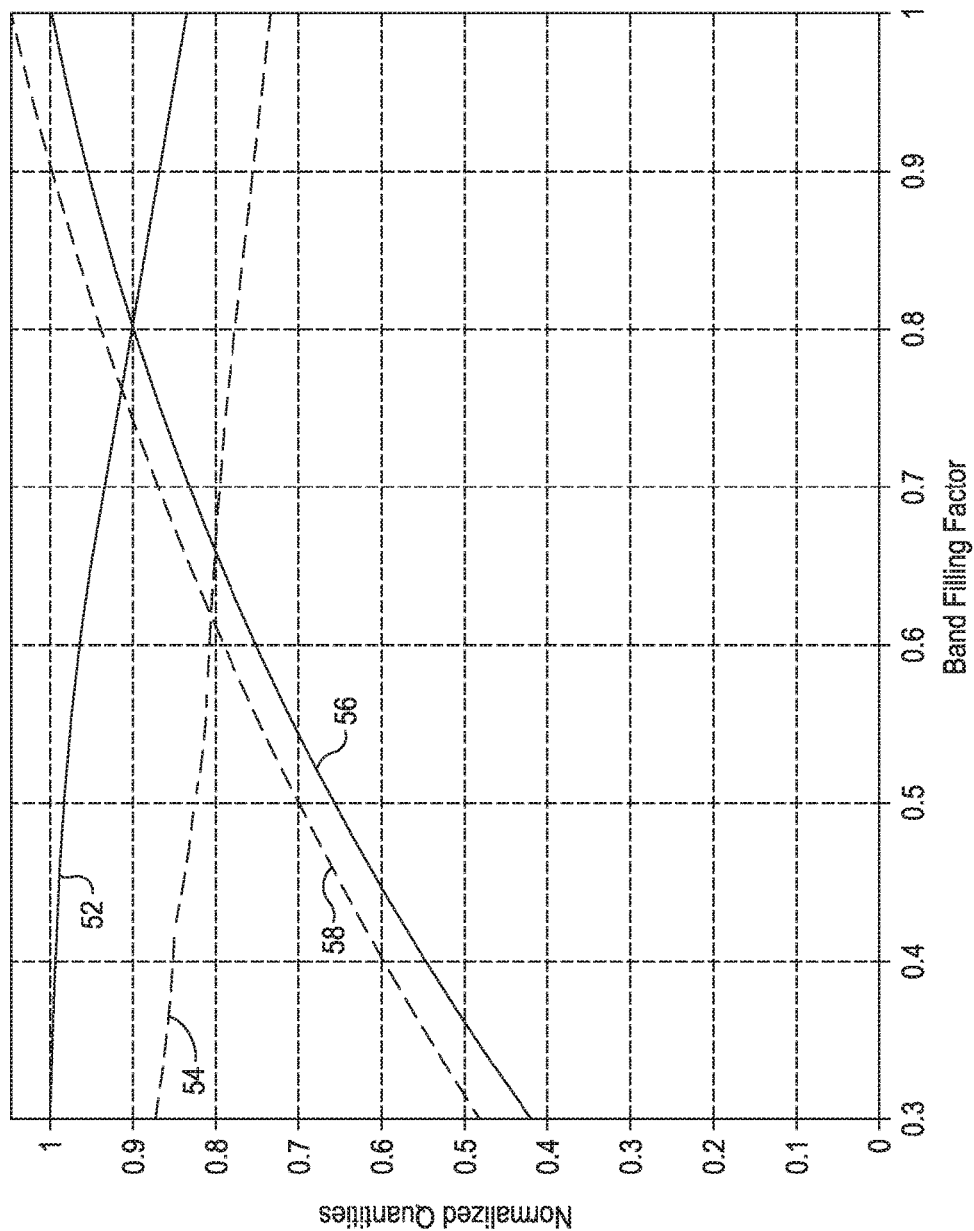
FIG. 7 provides a plot of the NMR signal loss and SNR/√time for the shaped pulse and the rectangular pulse.

FIG. 7 shows NMR signal loss and the SNR/√time for the shaped pulse and the rectangular pulse. Plots 52 (shaped pulse) and 54 (rectangular pulse) represent comparison for the NMR signal loss demonstrating greater loss for the rectangular pulse. The comparison illustrates the fact that rectangular pulse has much stronger side-lobes of the frequency spectrum and therefore stronger inter-band interference.

Plots 56 and 58 provide the SNR/√time ratio for shaped pulse and rectangular pulse, respectively, demonstrating an advantage of the rectangular over the shaped pulse despite stronger interference in case of rectangular pulse. The greater SNR/√time ratio for the rectangular pulse may be because the rectangular pulse is twice shorter than the shaped pulse. Therefore, the minimum achievable echo spacing is smaller.

These numerical simulations demonstrate that tighter band packing offers SNR and SNR/√time benefits in multi-frequency NMR measurements. Additionally, the numerical simulation illustrate that rectangular pulses, which allow for shorter echo spacing, provides greater SNR and SNR/√time.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A gradient multi-frequency nuclear magnetic resonance (NMR) method comprising:
    selecting at least a first and second frequencies and a time interval that increases a band packing density to allow for increased interference between a first sequence of radio frequency (RF) pulses at the first frequency and second NMR spin echoes generated in response to a second sequence of RF pulses at the second frequency;
    applying, with an NMR logging tool disposed in a wellbore penetrating a subterranean formation, the first sequence of RF pulses at the first frequency to interrogate a first sensitive volume of the subterranean formation;
    acquiring first NMR relaxation data corresponding to the first sensitive volume of the subterranean formation;
    applying, with the NMR logging tool, the second sequence of RF pulses at the second frequency to interrogate a second sensitive volume of the subterranean formation, the second sequence being applied at the time interval following the first sequence; and
    acquiring second NMR relaxation data corresponding to the second sensitive volume of the subterranean formation.

2. The method of claim 1 further comprising:
    measuring tool motion with a sensor coupled to the NMR logging tool;
    calculating a tool motion correction based on the tool motion; and
    applying the tool motion correction to at least the first NMR relaxation data.

3. The method of claim 1, wherein the first sequence and the second sequence of RF pulses comprise rectangular RF pulses with a band filling factor of about 0.5 to about 1.0.

4. The method of claim 1, wherein the first sequence and the second sequence of RF pulses comprise non-rectangular RF pulses with a band filling factor of about 0.6 to about 1.0.

5. The method of claim 1, wherein the first sequence and the second sequence of RF pulses are Carr-Purcell-Meiboom-Gill pulse sequences.

6. The method of claim 1 further comprising:
    comparing an amplitude of the first and second NMR relaxation data corresponding to the first and second sensitive volumes; and
    calculating a permeability of the subterranean formation.

7. The method of claim 1, wherein the time interval is a first time interval and the method further comprises:
    selecting a third frequency and a second time interval to allow for interference between the second sequence of RF pulses and third NMR spin echoes corresponding to a third sensitive volume in the subterranean formation;
    applying a third sequence of RF pulses at the third frequency to interrogate the third sensitive volume of the subterranean formation, the third sequence being applied at the second time interval following the second sequence; and
    acquiring third NMR relaxation data corresponding to the third sensitive volume of the subterranean formation.

8. The method of claim 7 further comprising:
    comparing an amplitude of the first and third NMR relaxation data corresponding to the first and third sensitive volumes; and
    calculating a permeability of the subterranean formation.

9. The method of claim 7, wherein the first, second, and third sequences of RF pulses comprise rectangular RF pulses with a band filling factor of about 0.5 to about 1.0.

10. The method of claim 7, wherein the first, second, and third sequences of RF pulses comprise non-rectangular RF pulses with a band filling factor of about 0.6 to about 1.0.

11. The method of claim 1, wherein selecting at least the first and second frequencies and the time interval increases at least one of a signal-to-noise ratio of NMR relaxation data and a signal-to-noise ratio per square root of time of NMR relaxation data.

12. A method comprising:
    performing a gradient multi-frequency nuclear magnetic resonance (NMR) procedure with an NMR logging tool disposed in a wellbore penetrating a subterranean formation and thereby obtaining NMR relaxation data, the gradient multi-frequency NMR procedure comprising:
    applying a sequence of rectangular radio-frequency (RF) pulses at two or more frequencies with a band filling factor of about 0.5 to about 1.0, each of the frequencies corresponding to a sensitive volume of the subterranean formation; and
    acquiring the NMR relaxation data corresponding to each sensitive volume of the subterranean formation.

13. The method of claim 12, wherein applying the sequence of rectangular RF pulse sequences includes a Carr-Purcell-Meiboom-Gill pulse sequence at each of the frequencies.

14. The method of claim 12 further comprising:
    measuring tool motion with a sensor coupled to the NMR logging tool;
    calculating a tool motion correction based on the tool motion; and
    applying the tool motion correction to the NMR relaxation data.

15. The method of claim 12 further comprising:
    comparing an amplitude of the NMR relaxation data corresponding to a first volume and a second sensitive volume; and
    calculating a permeability of the subterranean formation.

16. A method comprising:
    performing a gradient multi-frequency nuclear magnetic resonance (NMR) procedure with an NMR logging tool disposed in a wellbore penetrating a subterranean formation and thereby obtaining NMR relaxation data, the gradient multi-frequency NMR procedure comprising:
    applying a sequence of non-rectangular radio-frequency (RF) pulse sequences at two or more frequencies with a band filling factor of about 0.6 to about 1.0, each of the frequencies corresponding to a sensitive volume of the subterranean formation; and
    acquiring the NMR relaxation data corresponding to each sensitive volume of the subterranean formation.

17. The method of claim 16, wherein applying the sequence of nonrectangular RF pulse sequences includes a Carr-Purcell-Meiboom-Gill pulse sequence at each of the frequencies.

18. The method of claim 16 further comprising:
    measuring tool motion with a sensor coupled to the NMR logging tool;

calculating a tool motion correction based on the tool motion; and applying the tool motion correction to the NMR relaxation data.

19. The method of claim 16 further comprising:

comparing an amplitude of the NMR relaxation data corresponding to a first volume and a second sensitive volume; and calculating a permeability of the subterranean formation.

* * * * *